(12) United States Patent
Kanios et al.

(10) Patent No.: US 6,337,086 B1
(45) Date of Patent: Jan. 8, 2002

(54) PRESSURE SENSITIVE ADHESIVE COMPOSITIONS FOR TRANSDERMAL DRUG DELIVERY DEVICES

(75) Inventors: David Paul Kanios; Juan Mantelle, both of Miami, FL (US); Linda Sue Nartker; Victor Albert Raul, both of Midland, MI (US); Katherine Lynn Ulman, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/245,687

(22) Filed: Feb. 6, 1999

(51) Int. Cl.[7] .............................. A61K 9/70; A61K 9/14; A61F 13/00
(52) U.S. Cl. ........................................ 424/449; 424/448
(58) Field of Search .................................. 424/448, 449

(56) References Cited

U.S. PATENT DOCUMENTS

| | | | |
|---|---|---|---|
| 4,584,355 A | 4/1986 | Blizzard | 525/477 |
| 4,585,836 A | 4/1986 | Homan | 525/477 |
| 4,591,622 A | 5/1986 | Blizzard | 525/477 |
| 4,615,699 A | 10/1986 | Gale | 604/897 |
| 4,655,767 A | 4/1987 | Woodard | 604/896 |
| 4,814,168 A | 3/1989 | Sablotsky | 424/78 |
| 4,994,267 A | 2/1991 | Sablotsky | 424/78 |
| 4,994,278 A | 2/1991 | Sablotsky | 424/449 |
| 5,006,108 A | 4/1991 | LaPrade | 604/20 |
| 5,032,207 A | 7/1991 | Sablotsky | 156/250 |
| 5,234,957 A | 8/1993 | Mantelle | 514/772.6 |
| 5,300,291 A | 4/1994 | Sablotsky | 424/78.18 |
| 5,332,576 A | 7/1994 | Mantelle | 424/443 |
| 5,405,486 A | 4/1995 | Sablotsky | 156/510 |
| 5,446,070 A | 8/1995 | Mantelle | 514/772.6 |
| 5,474,783 A | 12/1995 | Miranda | 424/448 |
| RE35,474 E * | 3/1997 | Woodard et al. | 424/448 |
| 5,656,285 A | 8/1997 | Sablotsky | 424/448 |
| 5,656,286 A | 8/1997 | Miranda | 424/449 |
| 5,686,099 A | 11/1997 | Sablotsky | 424/449 |
| 5,719,197 A | 2/1998 | Kanios | 514/772.6 |
| 5,725,876 A | 3/1998 | Mantelle | 424/449 |

* cited by examiner

*Primary Examiner*—Shelley A. Dodson
(74) *Attorney, Agent, or Firm*—Roger E. Gobrogge (57) ABSTRACT

A transdermal drug delivery device for the controlled transdermal delivery of an active pharmaceutical agent. The device comprises a drug delivery device comprising an active pharmaceutical agent and a means for its controlled delivery through the skin; and (B) a silicone pressure sensitive adhesive for maintaining contact between the device and the skin of a wearer. The silicone pressure sensitive adhesive comprises silicone resin copolymer and a polydiorganosiloxane and has a silanol concentration in the range of between about 8000 and about 13,000 ppm. The present invention also relates to methods for producing the above silicone pressure sensitive adhesive compositions.

9 Claims, 1 Drawing Sheet

FIG. 1

PRESSURE SENSITIVE ADHESIVE COMPOSITIONS FOR TRANSDERMAL DRUG DELIVERY DEVICES

BACKGROUND OF THE INVENTION

This invention relates to a transdermal drug delivery device for the controlled release of a pharmaceutical agent which contains a silicone skin contact pressure-sensitive adhesive made from an adhesive composition which contains a well defined concentration of silanol such that it remains adherent to the skin.

Pressure sensitive adhesive (PSA) compositions are well known in the art and many are commercially available. Generally, silicone PSA's are produced by either blending or condensing a silicone resin and a polydiorganosiloxane. These types of silicone pressure sensitive adhesives have been disclosed for example in U.S. Pat. Nos. 2,736,721, 2,814,601, 2,857,356, and 3,528,940. The adhesion of such materials can be varied by altering the ratio of units in the resinous material or the ratio of resin to polydiorganosiloxane.

The use of silicone based PSAs in transdermal drug delivery devices is also known in the art. Examples of such devices can be found in U.S. Pat. Nos. 3,731,683 (Zaffaroni); U.S. Pat. No. 3,797,494 (Zaffaroni); U.S. Pat. No. 4,031,894 (Uhrquhart, et al.) and U.S. Pat. No. 4,336,243 (Sanvordeker, et al.). Such devices are held in contact with the skin by means of a pressure-sensitive adhesive and the devices are typically intended to be left in contact with the skin for a period of 24 hours or more. In view of the extended period of contact with the skin, the adhesive should be capable of adhering to the skin for at least that length of time and should also be reasonably non-irritating and non-sensitizing to the skin.

Silicone pressure-sensitive adhesives are known to be non-irritating and non-sensitizing to the skin and have been used as adhesives for certain devices such as those for the controlled release of nitroglycerine. Silicone PSAs are known in the art and are commercially available.

U.S. Pat. No. RE 35,474 teaches a transdermal drug delivery device for the controlled delivery of amino-functional drugs. This patent teaches that aminofunctional drugs interfere with the properties of PSAs by catalyzing the reaction of silicon bonded hydroxyl (silanol) groups and, thereby, cause increased increase shear of the PSA material and, thus, loss of tack during storage. The reference teaches that this effect can be inhibited by chemically treating the PSAs with an agent which reduces their silanol content. This patent, however, teaches that the amount of agent used to treat the PSA must be an amount of at least 0.8 moles triorganosilyl units for every mole of silanol. This amount of treating agent generally reduces the silanol concentration of the PSA to levels below about 7700. The present inventors, however, have now discovered that when the silanol content is too low, further crosslinking of the adhesive network is sufficiently reduced and this loosely crosslinked network becomes plasticized and oozy, thus resulting in poor PSA quality.

Accordingly, one of the objects of the present invention is to provide silicone PSAs having a low, but well defined concentrations of silanol are useful in transdermaldrug delivery device applications.

SUMMARY OF THE INVENTION

The present invention relates to a transdermal drug delivery device for the controlled transdermal delivery of an active pharmaceutical agent. The device comprises (A) a drug delivery device comprising an active pharmaceutical agent and a means for its controlled delivery through the skin; and (B) a silicone pressure sensitive adhesive for maintaining contact between the device and the skin of a wearer. The silicone pressure sensitive adhesive comprises (i) between about 40 and about 70 parts by weight of at least one resin copolymer comprising triorganosiloxy units of the formula $R_3SiO_{1/2}$ and tetrafunctional siloxy units of the formula $SiO_{4/2}$ in a ratio of about 0.6 to 0.9 triorganosiloxy units for each tetrafunctional siloxy unit and (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms. The silanol content of the silicone pressure sensitive adhesive composition is reduced by chemically treating at least a portion of (i), (ii) or the mixture of (i) and (ii) with at least one chemical treating agent (iii) that reacts with silicon-bonded hydroxyl groups to reduce the silicon-bonded hydroxyl content of the composition to a range of between about 8000 and about 13,000.

The present invention also relates to methods for producing the above silicone pressure sensitive adhesive compositions.

DETAILED DESCRIPTION OF THE INVENTION

The present invention is based on the unexpected discovery that silicone pressure sensitive adhesive (PSA) compositions must contain a certain concentration of silicon bonded hydroxyl groups (silanol) to be useful for certain applications. Specifically, when silicone PSAs are used in transdermal drug delivery devices, the silanol content of the PSA must be adjusted based on the active pharmaceutical agent to ensure that the adhesive strength remains acceptable over time. When the silanol content of the adhesive is too high, the drug can cause the silanols to condense, resulting in increased shear of the adhesive and, thus, decreased adhesive strength. When the silanol content of the adhesive is too low, on the other hand, there is little crosslinking of the adhesive network and the materials is plasticized (softened) to too high a degree, thus resulting in unwanted flow (cold flow).

The transdermal drug delivery devices used in the present invention are not critical and many such devices are known in the art and are available commercially. Generally, they comprise an active pharmaceutical agent (drug) and a means for its controlled delivery through the skin. In one generic embodiment, the device can comprise a suitable reservoir for holding the drug and the means for controllably releasing the drug. In another embodiment, the device can comprise a matrix, such as, for example, the drug and the PSA or a layered matrix such as, for example, a matrix with a layer of the PSA. Similarly, the device could be an elastomeric body (which could be adhesive in nature) impregnated with a drug, wherein the elastomer matrix controls the release of the drug.

Generally, one surface of the transdermal drug delivery device is coated with a silicone pressure-sensitive adhesive to maintain the device in contact with the skin of the wearer. If desired, a backing material comprising a conventional drug impermeable film coated with a conventional release coating for silicone PSAs can be applied over the silicone PSA during storage.

When the device coated with the silicone PSA comes in contact with the skin, the drug diffuses from the device, including the PSA, at a controlled rate and permeates through the epidermis into the dermis. This diffusion-permeation process allows the drug device to maintain a therapeutic concentration for 24 hours or more. As such, it can be seen that the drug will come into contact with the silicone PSA and, thus, may cause untoward reactions.

As is well known to those skilled in the art, other types of transdermal drug delivery devices are available and, with the exception of a drug in combination with silicone PSAs as will be described in more detail below, the form of the transdermal drug delivery device and means by which the delivery of such drugs are controlled are not critical. For example, the elastomeric body could be replaced by a solution of the drug to be delivered contained within a container comprising a semipermeable membrane which controls the release rate of the drug to the skin. The aforementioned patents to Zaffaroni, Uhrquhart, et al. and Sandvordeker, et al. describe other types of transdermal drug delivery devices employing PSAs and are hereby incorporated by reference to teach other examples of transdermal drug delivery devices which may find use in the present invention.

A silicone PSA is used in the present invention because of its biocompatibility. This silicone PSA composition comprises (i) between about 40 and about 70 parts by weight of at least one resin copolymer comprising triorganosiloxy units of the formula $R_3SiO1/2$ and tetrafunctional siloxy units of the formula $SiO_{4/2}$ in a ratio of about 0.6 to 0.9 triorganosiloxy units for each tetrafunctional siloxy unit and (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms. The silanol content of the silicone PSA composition is reduced by chemically treating at least a portion of (i), (ii) or the mixture of (i) and (ii) with at least one chemical treating agent (iii) that reacts with silicon-bonded hydroxyl groups to reduce the silicon-bonded hydroxyl content of the composition to a range of between about 8000 and about 13,000 and, thereby, insure sufficient adherence over time.

As used herein, "sufficient adherence" is intended to mean that the device is sufficiently tacky to the touch to be able to adhere instantly to the skin after application to the skin without an undue mount of pressure being exerted against the device to get it to adhere to the skin.

The active pharmaceutical agents to be delivered for therapeutic purposes can be those which are amenable to being delivered transdermally and which interact with the silicone PSA to modified its adherence over time. Examples of such agents include nitroglycerine, fentanyl, scopolamine, hormones such as estrogen and testosterone, clonidine, nicotine, and tetracain. Other examples of drugs for use in transdermal drug delivery systems will be apparent to those skilled in the art. See, for example, the Zaffaroni patents cited above and pages 149–217 Yie Chien's treatise entitled "Novel Drug Delivery Systems" which is Volume 14 of Drugs and the Pharmaceutical Sciences, Marcel Dekker, Inc., New York, N.Y. 10016 (1982) for further information on drugs suitable for transdermal delivery.

Without wishing to be bound by a theory, it is postulated that certain drugs act as catalysts for the condensation of silicon-bonded hydroxyl groups in silicone pressure-sensitive adhesives. See Canadian Pat. No. 575,664 to Bartell (issued May 12, 1959) and British Pat. No. 859,511 to Lamason (published Jan. 25, 1961). Thus, these drugs are also capable of causing silicone PSAs, containing a sufficient level of silicon-bonded hydroxyl radicals, to condense and thereby lose their tack and their ability to have sufficient adherence to the skin upon aging. Loss of tack is particularly noticeable when the tack value of the adhesive is desired to be relatively low (<1100 g/cm$^2$) to avoid damage to the skin. Generally, one observes greater detrimental effects on tack and other physical properties of the PSA compositions with adhesives having lower tack values ("drier adhesives" where the term "dry" means no tack to a light touch) and higher resin copolymer contents.

By the same token, it has been noted by the present inventors that when one attempts to remedy this interaction by lowering the silanol content, too low a concentration results in cold flow.

Consequently, the present inventors have discovered that silicone PSAs with well defined silanol concentrations are often desired for certain drugs. The silanol concentration in these PSAs can be adjusted by chemically treating the resin copolymer, the polydiorganosiloxane, or the mixture of these materials. Likewise, the desired silanol concentration can be achieved by blending a PSA having a substantial silanol concentration with a PSA having a reduced silanol concentration as disclosed below.

The silicone PSA compositions preferred for use in the method and device of the present invention are described in U.S. Pat. Nos. 4,591,622, 4,584,355, and 4,585,836 which are hereby incorporated by reference. Any adhesives used for this purpose must, of course, be biocompatible and that can be evaluated by the use of standard testing procedures.

The manner for preparing preferred silicone PSAs by the process of 4,591,622 will now be described. This process can be used to prepare silicone PSAs having a silanol concentration in the range claimed in the present invention or, alternatively, the process can be used to prepare silicone PSAs having a greatly reduced silanol concentration which can be mixed with silicone PSAs having higher silanol concentrations to arrive at the range claimed herein. Further details and examples of compositions can be found in the aforementioned patents.

One type of silicone PSA composition employs a composition made by the method comprising the steps of:

(I) mixing (i) from 40 to 70 inclusive parts by weight of at least one resin copolymer containing silicon-bonded hydroxyl radicals and consisting essentially of R3SiO1/2 units and SiO4/2 units in a mole ratio of 0.6 to 0.9 $R_3SiO_{1/2}$ units for each $SiO_{4/2}$ unit present, (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is a monovalent organic radical selected from the group consisting of hydrocarbon radicals of from 1 to 6 inclusive carbon atoms, each A radical is independently selected from R or halohydrocarbon radicals having from 1 to 6 inclusive carbon atoms, each T radical is independently selected from the group consisting of R, OH, H or OR', and each R' is independently an alkyl radical of from 1 to 4 inclusive carbon atoms; a sufficient amount of at least one organosilicon endblocking agent (iii) capable of generating an endblocking triorganosilyl unit to provide a silanol concentration in the range of 8000 to 13,000, (iv) when desirable, an additional catalytic amount of a mild silanol condensation catalyst in the event that none is provided by said (ii), and (v) when necessary, an effective mount of an organic solvent which is inert with respect to (i), (ii), (iii) and (iv) to reduce the viscosity of a mixture of (i), (ii), (iii), and (iv), and (II) condensing the mixture of (i), (ii), (iii) and (iv) at least until a substantial amount of the endblocking triorganosilyl units have reacted with the silicon-bonded hydroxyl radicals and T radicals of said (i) and (ii). Examples of the organosilicon endblocking agent capable of generating an endblocking triorganosilyl unit are described in U.S. Pat. No. 4,591,622 and U.S. Reissue Pat. No. RE35,474, which are hereby incorporated by reference.

The pressure-sensitive adhesive compositions are made in accordance with the present invention using from 40 to 70 inclusive parts by weight of silicone copolymer resins (i) and from 30 to 60 parts by weight of polydiorganosiloxane (ii) of the type which have been used in the past to make such compositions. More preferred are compositions employing from 50 to 65 parts by weight of resin copolymer (i) and from 35 to 50 parts by weight of polydiorganosiloxane (ii).

The silicone resin copolymers (i) are well-known materials. They contain silicon-bonded hydroxyl radicals in amounts which typically range from about 1 to 4 weight percent of silicon-bonded hydroxyl radicals and comprise triorganosiloxy units of the formula $R_3SiO_{1/2}$ and tetrafunctional siloxy units of the formula $SiO_{4/2}$ in a mole ratio of from 0.6 to 0.9 $R_3Si_{1/2}$ units for each $SiO_{4/2}$ unit present. Blends of two or more such copolymers may also be used. There should be at least some and preferably at least 0.5% silicon-bonded hydroxyl content to enable the polydiorganosiloxane component to copolymerize with the copolymer resin and/or to react with the endblocking agent being added to chemically treat the silicone pressure-sensitive adhesive composition. These resin copolymers are generally benzene-soluble resinous materials which are typically solids at room temperature and are prepared as, and usually, but not necessarily used as, a solution in an organic solvent. Typical organic solvents used to dissolve resin copolymer (i) include benzene, toluene, xylene, methylene chloride, perchloroethylene, naphtha mineral spirits and mixtures of these.

Resin copolymer (i) consists essentially of from 0.6 to 0.9 $R_3SiO_{1/2}$ units for every $SiO_{4/2}$ unit in the copolymer. There may also be a few mole percent of $R_2SiO$ units present in the copolymer provided that the presence of such units does not cause the ultimate product of this process to lose its ability to function as a PSA. Each R denotes, independently, a monovalent hydrocarbon radical having from 1 to 6 inclusive carbon atoms such as methyl, ethyl, propyl, isopropyl, hexyl, cyclohexyl, vinyl, allyl, propenyl and phenyl. Preferably, the $R_3SiO_{1/2}$ units are $Me_3SiO_{1/2}$ units and/or $Me_2R^1SiO_{1/2}$ units wherein is $R^1$ is a vinyl ("Vi") or phenyl ("Ph") radical. More preferably, no more than 10 mole percent of the $R_3SiO_{1/2}$ units present in resin copolymer (i) are $Me_2R^2SiO_{1/2}$ units and the remaining units are $Me_3SiO_{1/2}$ units where each $R^2$ is a vinyl radical. Most preferably, the $R_3SiO_{1/2}$ units are $Me_3SiO_{1/2}$ units.

The mole ratio of $R_3SiO_{1/2}$ and $SiO_{4/2}$ units can be determined simply from a knowledge of the identity of the R radicals in the $R_3SiO_{1/2}$ units and the percent carbon analysis of the resin copolymer. In the preferred resin copolymer consisting of from 0.6 to 0.9 $Me_3SiO_{1/2}$ units for every $SiO_{4/2}$ unit, the carbon analysis has a value of from 19.8 to 24.4 percent by weight.

Resin copolymer (i) may be prepared according to Daudt et al., U.S. Pat. No. 2,676,182 (issued Apr. 20, 1954 and hereby incorporated by reference) whereby a silica hydrosol is treated at a low pH with a source of R3SiO1/2 units such as a hexaorganodisiloxane such as $Me_3SiOSiMe_3$, $ViMe_2SiOSiMe_2Vi$ or $MeViPhSiOSiPhViMe$ or triorganosilane such as $Me_3SiCl$, $Me_2ViSiCl$ or $MeViPhSiCl$. Such copolymer resins are typically made such that the copolymer resin contains about 1 to 4 weight percent of silicon-bonded hydroxyl radicals. Alternatively, a mixture of suitable hydrolyzable silanes free of R radicals may be cohydrolyzed and condensed. In this alternative procedure, it is a typical practice to further treat the copolymer product with a suitable silylating agent, such as hexamethyldisilazane or divinyltetramethyldisilazane, to reduce the silicon-bonded hydroxyl content of the copolymer product to less that 1 percent by weight. This step would not be necessary, but could be used, in the process now being described. Preferably, the resin copolymers employed contain from about 1 to 4 weight percent of silicon-bonded hydroxyl radicals.

Ingredient (ii) is also a well-known material and is one or more polydiorganosiloxanes comprising ARSiO units terminated with endblocking $TRASiO_{1/2}$ units, each of which polydiorganosiloxanes has a viscosity of from 100 centipoise to 30,000,000 centipoise at 25° C. (100 millipascal-seconds to 30,000 pascal seconds (Pa.s) where 1 centipoise equals 1 millipascal second). As is well-known, viscosity is directly related to the average number of diorganosiloxane units present for a series of polydiorganosiloxanes of varying molecular weights which have the same endblocking units. Polydiorganosiloxanes having a viscosity of from about 100 to 100,000 centipoise at 25° C. range from fluids to somewhat viscous polymers. These polydiorganosiloxanes are preferably prereacted with resin copolymer (i) prior to condensation in the presence of endblocking agent (iii) to improve the tack and adhesion properties of the resulting PSA as will be further described. Polydiorganosiloxanes having viscosities in excess of 100,000 centipoise can typically be subjected to the condensation/endblocking step (II) of the present invention without prereaction. Polydiorganosiloxanes having viscosities in excess of 1,000,000 centipoise are highly viscous products often referred to as gums and the viscosity is often expressed in terms of a Williams Plasticity value (polydimethylsiloxane gums of about 10,000,000 centipoise viscosity typically have a Williams Plasticity Value of about 50 mils (1.27 mm) or more at 25° C.).

The polydiorganosiloxanes of (ii) consist essentially of ARSiO units where each R is as defined above. Each A radical is selected from radicals such as R or halohydrocarbon radicals of from 1 to 6 inclusive carbon atoms such a chloromethyl, chloropropyl, 1-chloro-2-methylpropyl, 3,3, 3-trifluoropropyl and $F_3C(CH_2)_5$ radicals. Thus the polydiorganosiloxane can contain $Me_2SiO$ units, PhMeSiO units, MeViSiO units, $Ph_2SiO$ units, methylethylsiloxy units, 3,3,3-trifluoropropyl units and 1-chloro, 2-methylpropyl units and the like. Preferably, the ARSiO units are selected from the group consisting of $R_2SiO$ RR'SiO units, $Ph_2SiO$ units and combinations of both where R and R' are as above, at least 50 mole percent of the R' radicals present in the polydiorganosiloxane (ii) are methyl radicals and no more than 50 mole percent of the total moles of ARSiO units present in each polydiorganosiloxane of (ii) are $Ph_2SiO$ units. More preferably, no more than 10 mole percent of the ARSiO units present in each polydiorganosiloxane (ii) are MeRSiO units where R is as above defined and the remaining ARSiO units present in each polydiorganosiloxane are $Me_2SiO$ units. Most preferably, substantially all of the ARSiO units are $Me_2SiO$ units.

Each polydiorganosiloxane (ii) is terminated with endblocking units of the unit formula $TRASiO_{1/2}$ where R and A are as defined above and each T radical is R, OH, H or OR' radicals where each R' is an alkyl radical of from 1 to 4 inclusive carbon atoms such as methyl, ethyl, n-propyl, and isobutyl radicals. H, OH and OR' provide a site for reaction with the endblocking triorganosilyl units of ingredient (iii) and also provide a site for condensation with other such radicals on polydiorganosiloxanes (ii) or with the silicon-bonded hydroxyl groups present in resin copolymer (i). Use of polydiorganosiloxanes where T is OH is most preferred because the polydiorganosiloxane (ii) can then readily copolymerize with the resin copolymer (i). When an appropriate catalyst such as HCl, which is generated when chlorosilanes are used, or ammonia, which is generated when organosilazanes are used, as endblocking agents, then triorganosiloxy (e.g., $R_3SiO_{1/2}$ such as $(CH_3)_3SiO_{1/2}$ or $CH_2CH(CH_3)_2SiO_{1/2}$) unit terminated polydiorganosiloxanes can be employed because some of the triorganosiloxy units can be cleaved when the condensation reaction is conducted with heating. The cleavage exposes a silicon-bonded hydroxyl radical which can then condense with silicon-bonded hydroxyl radicals in the copolymer resin, with endblocking triorganosilyl units or with other polydiorganosiloxanes containing H, OH or OR' radicals or silicon-bonded hydroxyl radicals exposed by cleavage reactions. Mixtures of polydiorganosiloxanes containing different substituent radicals may also be used.

Methods for the manufacture of such polydiorganosiloxanes are well known as exemplified by the following U.S. Pat. Nos.: 2,490,357 (Hyde); U.S. Pat. 2,542,334 (Hyde); U.S. Pat. No. 2,927,907 (Polmanteer); U.S. Pat. No. 3,002,951 (Johannson); U.S. Pat. No. 3,161,614 (Brown, et al.); U.S. Pat. No. 3,186,967 (Nitzche, et al.); U.S. Pat. No. 3,509,191 (Atwell) and U.S. Pat. No. 3,697,473 (Polmanteer, et al.) which are hereby incorporated by reference.

To obtain PSAs which are to be cured by peroxide or through aliphatically unsaturated radicals present in resin copolymer (i) or polydiorganosiloxane (ii), if resin copolymer (i) contains aliphatically unsaturated radicals, then polydiorganosiloxane (ii) should be free of such radicals and vice-versa. If both components contain aliphatically unsaturated radicals, curing through such radicals can result in products which do not act as PSAs.

The distinguishing feature of the present invention is that the silicone PSA has a well defined silanol concentration in a range of between about 8000 and about 13,000. This can be accomplished by treating the above compositions of the invention with an agent which reacts with silanol or it can be accomplished by blending the above silicone PSAs with silicone PSAs which have a lower silanol content, such as those disclosed in U.S. Pat. No. RE35,474.

If the silanol content is reduced by chemically treating the compositions, this can be accomplished by treating the resin copolymer (i), by treating the polydiorganosiloxane (ii), by treating both the resin copolymer (i) and the polydiorganosiloxane (ii), and/or by treating a mixture of the resin copolymer (i) and the polydiorganosiloxane (ii).

The chemical treatment is preferably accomplished by conducting the condensation of resin copolymer (i) and polydiorganosiloxane (ii) in the presence of at least one organosilicon endblocking agent (iii) capable of generating endblocking triorganosilyl units. Examples of these endblocking agents are set forth in U.S. Pat. No. 4,591,622 and U.S. Reissue Pat. RE35,474 which are incorporated herein by reference.

Endblocking agents capable of providing endblocking triorganosilyl units are commonly employed as silylating agents and a wide variety of such agents are known. A single endblocking agent such as hexamethyldisilazane can be employed or a mixture of such agents such as hexamethyldisilazane and sym-tetramethyldivinyldisilazane can be employed to vary the physical properties of the PSA film. For example, use of an endblocking agent containing fluorinated triorganosilyl units such as $[(CF_3CH_2CH_2)Me_2Si]_2NH$ in the process of the present invention could result in a silicone PSA having improved resistance to hydrocarbon solvents after the film is deposited and the presence of the fluorinated triorganosilyl units could affect the tack and adhesion properties of the PSA when the R radicals present in the resin copolymer (i) and the polydiorganosiloxane (ii) are substantially composed of methyl radicals. By employing endblocking agents containing higher carbon content silicon-bonded organic radicals such as ethyl, propyl or hexyl radicals, the compatibility of the silicone PSA with organic PSAs could be improved to allow blending of such adhesives to obtain improved adhesive compositions. Use of endblocking agents having triorganosilyl units having organofunctional radicals such as amides, esters, ethers and cyano radicals could allow one to change the release properties of a PSA made in accordance with the present invention. Likewise, organofunctional radicals present in the PSA composition can be altered such as by hydrolyzing ROOCR radicals to generate HOOCR-radicals which are converted to MOOCR radicals where M is a metal cation such as lithium, potassium or sodium. The resulting composition may then exhibit release or other properties different from a composition containing RCOOR-radicals.

Use of endblocking agents containing triorganosilyl units with unsaturated organic radicals such as vinyl can produce silicone PSAs which can be cross-linked through such groups. For example, an organosilicon cross-linking compound containing silicon-bonded hydrogen radicals can be added along with a noble metal such as a platinum metal or rhodium metal catalyst to a silicone PSA composition made in accordance with the present invention which contains PhMeViSi- and Me3Si-endblocking triorganosilyl units to produce a PSA composition which cures via the noble metal catalyzed addition of silicon-bonded hydrogen radicals to silicon-bonded vinyl radicals. Use of endblocking agents containing triorganosilyl units with phenyl radicals could improve the stability of the PSA to heat.

Thus, the endblocking agent serves several purposes in the present invention because it removes silicon-bonded hydroxyl radicals which can affect the stability of the resulting PSA with respect to the drugs, it enables one to modify the properties of the adhesive without making substantial changes in the resin copolymer and polydiorganosiloxanes and by selecting an appropriate level of endblocking agent, and one can alter the molecular weight and thereby the properties of the condensation product of the resin copolymer (i) and polydiorganosiloxane (ii) since the triorganosilyl units act as endblocking units.

In order to achieve the above, one must add at least a sufficient amount of one or more endblocking agents to provide a silanol concentration in the range of about 8000 to about 13,000. The resin copolymer (i) will typically contain the majority of the silicon-bonded hydroxyl content present in the combination of resin copolymer (i) and polydiorganosiloxane (ii).

When one desires to alter the properties of the PSA by including endblocking agents with specific radicals, it is desirable to use a resin copolymer (i) that has a higher silicon-bonded hydroxyl content (e.g., 1–4 weight percent) so that more of the triorganosilyl units confining such radicals will be reacted into the condensation product of resin copolymer (i) and polydiorganosiloxane (ii).

Examples of endblocking agents are (Me3Si)2NH, (ViMe2Si)2NH, (MePhViSi)2NH, (CF3CH2CH2Me2Si) 2NH, (Me3Si)2NMe, (ClCH2Me2Si)2NH, Me3SiOMe, Me3SiOC2H5, Ph3SiOC2H5, (C2H5)3SiOC2H5, Me2PhSiOC2H5, (i-C3H7)3SiOH, Me3Si(OC3H7), MePhViSiOMe, Me3SiCl, Me2ViSiCl, MePhViSiCl, (H2CCHCH2)Me2SiCl, (n-C3H7)3SiCl, (F3CCF2CF2CH2CH2)3SiCl, NCCH2CH2Me2SiCl, (n-C6H13)3SiCl, MePh2SiCl, Me3SiBr, (t-C4H9)Me2SiCl, CF3CH2CH2Me2SiCl, (Me3Si)2O, (Me2PhSi)2O, BrCH2Me2SiOSiMe3, (p-FC6H4Me2Si)2O, (CH3COOCH2Me2Si)2O, [(H2CCCH3COOCH2CH2) Me2Si]2O, [(CH3COOCH2CH2CH2)Me2Si]2O, [(C2H5OOCCH2CH2)Me2Si]2O, [(H2CCHCOOCH2) Me2Si]2O, (Me3Si)2S, (Me3Si)3N, Me3SiNHCONHSiMe3, F3CH2CH2Me2SiNMeCOCH3, (Me3Si)(C4H9)NCON(C2H5)2, (Me3Si)PhNCONHPh, Me3SiNHMe, Me3SiN(C2H5)2, Ph3SiNH2, Me3SiNHOCCH3, Me3SiOOCCH3, [(CH3CONHCH2CH2CH2)Me2Si]2O, Me3SiO(CH2) 4OSiMe3, Me3SiNHOCCH3, Me3SiCCH, HO(CH2) 4Me2Si]2O, (HOCH2CH2OCH2Me2Si)2O, H2N(CH2) 3Me2SiOCH3, CH3CH(CH2NH2)CH2Me2SiOCH3, C2H5NHCH2CH2S(CH2)6Me2SiOC2H5, HSCH2CH2NH (CH2)4Me2SiOC2H5, HOCH2CH2SCH2Me2SiOCH3.

Preferably, the endblocking agent employed is (Me3Si) 2NH.

A number of the above endblocking agents generate silanol condensation catalysts including acids such as hydrogen chloride and bases such as ammonia or amines when the triorganosilyl unit reacts with silicon-bonded hydroxyl radicals and/or H, OH or OR' radicals present in the resin copolymer (i) and polydiorganosiloxanes (ii). As will be further described, the condensation step (II) of the present invention is preferably done with heating and the presence of the catalyst causes the condensation of the resin copolymer (i) and polydiorganosiloxanes (ii) to take place at the same time that endblocking by the endblocking triorganosilyl units occurs. Depending on the method of manufacture employed, resin copolymer (i) and/or polydiorganosiloxane (ii) may contain a sufficient level of residual catalyst to effect condensation and endblocking. Thus, if desired, an additional catalytic amount of a "mild" silanol condensation catalyst (iv) can be used where the term "mild" means that it causes the endblocking agent to condense with the resin copolymer (i) and the polydiorganosiloxane (ii) while causing minimal siloxane bond rearrangement. Examples of "mild" catalysts are those known to be used as curing agents for PSA compositions including amines such as triethylamine and organic compounds such as tetramethylguanidine 2-ethylcaproate, tetramethylguanidine 2-ethylhexanoate and n-hexylamine 2-ethylcaproate. The additional catalyst (iv) selected should not cause an excessive amount of cleavage of siloxane bonds in the resin copolymer (i) and/or polydiorganosiloxane (iv) during the condensation reaction thereby resulting in gelation of the composition or a substantial loss of adhesive properties as is known to happen with organic tin catalysts and strong acids. Preferably, catalyst (iv) is only used when no catalyst is provided by endblocking agent (iii). Suitable catalysts and the selection of specific catalyst and amounts thereof for catalyzing the reaction of particular endblocking triorganosilyl units with the silicon-bonded hydroxyl radicals found on the organosiloxy units present in resin copolymer (i) and polydiorganosiloxane (ii) is known to those skilled in the art. Use of a catalyst such as HCl generated by a chlorosilane endblocking agent is preferable when $R_3SiO_{1/2}$ endblocking units are present in polydiorganosiloxane (ii) as noted earlier. Silazane endblocking agents can also be used when T is R and are preferred when T in the polydiorganosiloxane (ii) is H. Preferably, particularly when T in the polydiorganosiloxane (ii) is OH, an endblocking agent of the silazane type is used such that no extra catalyst needs to be added; the ammonia compound generated is generally volatile and can be eliminated more readily than a nonvolatile, solid catalyst material. When the resin copolymer (i) is prepared under acidic conditions as described in the Daudt, et al. patent above, there is often a sufficient level of acid catalyst present to enable endblocking units containing Y radicals of the alkoxy or OH type to be used without any further addition of a condensation catalyst.

When desirable, an effective amount of an organic solvent (v) can be added separately to the mixture of resin copolymer (i) (as a solid material or in organic solvent solution), polydiorganosiloxane (ii), endblocking agent (iii) and catalyst (iv) to reduce the viscosity thereof or else can be present as a result of the fact that (i) and/or (ii) was added as a solvent solution. The organic solvent should be inert towards the other components of the mixture and not react with them during the condensation step. As noted earlier, resin copolymer (i) is often made as a solvent solution in toluene or xylene. Use of an organic solvent is often necessary when polydiorganosiloxane (ii) is in the form of a high viscosity gum which results in a high viscosity mixture even when the mixture is heated to typical processing temperatures of 100°–150° C. Use of an organic solvent which permits azeotropic removal of water is preferred.

The term "organic solvent" includes a single solvent such as benzene, toluene, xylene, trichloroethylene, perchloroethylene, ketones, halogenated hydrocarbons such as dichlorodifluoromethane, naphtha mineral spirits and mixtures of two or more organic solvents to form a blended organic solvent. Use of a ketone such as methylisobutyl ketone as at least a portion of the solvent is preferred when fluorinated radicals are present on a major amount of the siloxane or silyl units present in polydiorganosiloxane (ii) for compatibility reasons. Preferably, the mixture contains a hydrocarbon solvent selected from the group consisting of benzene, toluene and xylene.

In accordance with step (I) of the present invention, resin copolymer (i), polydiorganosiloxane (ii), are mixed together with any organic solvent (v) that is to be added. While the condensation reaction may take place at room temperature if a suitably reactive silylating agent such as a silazane such as hexamethyldisilazane or a suitable catalyst such as tetramethylguanidine 2-ethyihexanoate is added and, optionally, with vacuum stripping of condensation by-products, the preferred method is to conduct the condensation reaction with heating and more preferably, at 100–120° C. Thus, the preferred method involves mixing (i), (ii) and (v) until the mixture is uniform followed by the addition of endblocking agent (iii) and, last, any condensation catalyst (iv) for the endblocking reaction to be added.

The condensation step (II) is begun when addition of a suitably reactive endblocking agent such as a silazane or a catalyst is made if the reaction is to take place at room temperature or else begins when the mixture is heated from 80° C. to 160° C., preferably at 100°–120° C. Condensation is preferably allowed to proceed at least until the rate of evolution of condensation byproducts such as water is substantially constant. Heating is then continued until the desired physical properties such as viscosity, tack and adhesion values are obtained. Typically the mixture is allowed to reflux for an additional 1 to 4 hours after the rate of evolution of condensation by-products is substantially constant. Longer condensation times may be needed for compositions containing organofunctional groups such as fluorinated radicals on the polydiorganosiloxane (ii) and/or endblocking agents which are less compatible with those present on the copolymer (i).

When the condensation reaction is complete, the residual endblocking agent is solvent stripped away by removing excess solvent during or after the azeotropic removal of condensation by-products. The nonvolatile solids content of the resulting silicone PSA composition can be adjusted by adding or removing solvent, the solvent present can be completely removed and a different organic solvent added to the silicone PSA product, the solvent can be removed completely if the condensation product is sufficiently low in viscosity or else the mixture can be recovered and used as is. Presently, it is preferred to have the PSA compositions in organic solvent solution wherein the organic solvent comprises from 30 to 70 weight percent of the total mixture of (i), (ii), (iii), (iv), and (v), particularly when the polydiorganosiloxane (ii) has a viscosity at 25° C. of greater than 100,000 centipoise.

The above procedure is preferred for compositions wherein the polydiorganosiloxanes (ii) are greater than about 100,000 centipoise in viscosity at 25° C. When the viscosity of the polydiorganosiloxanes (ii) are less than about 100,000 centipoise at 25° C., the physical properties of PSAs obtained therefrom are not always as high in tack and adhesion as may be desired and may also tend to result in adhesives possessing some adhesive transfer between substrates, see for example, the Pail Patent cited above.

For this reason, it is preferred that a precondensation step such as that employed in the Pail Patent be used in the process of the present invention prior to the condensation step in the presence of an endblocking agent (iii) be used when a substantial amount of the polydiorganosiloxanes (ii) have a viscosity of less than 100,000 centipoise at 25° C. In this case, Step (I) of the method of the present invention comprises the steps of (Ia) mixing resin copolymers (i), polydiorganosiloxanes (ii) and any organic solvent (v) together in the presence of a silanol condensation catalyst of the type previously described (anhydrous ammonia gas is presently preferred), (Ib) condensing (i) and (ii) to form a condensed product such as by heating under reflux conditions for 1 to 10 hours and (Ic) mixing the product of step (Ib) with (iii), (iv) and any further amount of organic solvent (v) which is necessary prior to proceeding with step (II) of the method of the present invention. The product of step (Ib) is thus increased in molecular weight by the precondensation step, but still contains residual silicon-bonded hydroxyl groups which can be endblocked in accordance with the present method of the invention to result in an improved PSA composition. The resulting silicone PSA composition is then processed according to Step (II) and the solvent can be adjusted as described above to obtain a finished silicone PSA composition.

When endblocking agents which generate ammonia upon reaction with silicon-bonded hydroxyl radicals such as those of the formula $(Me_3Si)_2NH$ are employed, it is preferred that residual ammonia generated by the endblocking agent be removed since the adhesive composition is to be used in a medical application. This can be accomplished in the manner described in U.S. Pat. No 4,584,355 by modifying the above-described method to employ the above ammonia generating endblocking agents and eliminating the use of optional condensation catalyst (iv) during the step involving condensation in the presence of the endblocking agent because the ammonia released functions as such a catalyst and further incorporating water as an ingredient as follows.

The manner of making compositions via the method of U.S. Pat. No. 4,584,355 includes the incorporation of about 0.5 to 10 moles of water per mole of NH provided by all endblocking agent (iii) present in the composition. 0.5 moles of water would be an effective minimum with the use of at least 1.0 moles of water being more preferred and higher levels such as at least 3 moles of water per mole of NH being preferred to obtain optimum removal of ammonia from the composition, particularly where the silicon-bonded hydroxyl content is from resin copolymer (i). Use of more than about 10 moles of water per mole of NH appears to be wasteful.

In the most preferred manner of making silicone PSA compositions wherein the aforementioned ammonia generating endblocking agents are employed, the method taught in U.S. Pat. No 4,585,836 is employed. However, if the adhesive composition is stripped of volatile solvents during processing, such as to substitute one solvent for another, use of alcohol as described in U.S. Pat. No 4,585,836 may not be needed. Use of the method of U.S. Pat. No. 4,584,355 which employs water to assist in the removal of residual ammonia from the adhesive compositions is effective for most purposes in practicing the present invention. This method is similar to that described above for U.S. Pat. No. 4,584,355 and includes the incorporation of 0.1 to 10 moles of water per mole of NH provided by all endblocking agent (iii) present in the composition. The amount of water added does not appear to be critical; 0.1 moles of water appears to be an effective minimum while more than about 10 moles of water per mole of NH appears to be wasteful.

U.S. Pat. No 4,585,836 further includes the use of from 0.001 to 10 parts by weight per 100 parts by weight of resin copolymer (i) and polydiorganosiloxane (ii) of at least one "ammonia scavenger compound". An "ammonia scavenger compound" is an organofunctional compound such as an alcohol which has one or more polar sites such as a hydroxyl radical and one or more non-polar sites. While not wishing to be limited to a particular theory of operation, the polar portion of the ammonia scavenger compound functions to associate with the ammonia generated by the endblocking agent more strongly than with the silicone portion of the composition to enable it to be removed from the composition when it is no longer needed. The ammonia scavenger compound must have a sufficiently non-polar character to enable that portion of the compound to associate with the non-polar portions of the silicone PSA composition to enable it to make its polar site available for association with the ammonia being released from the endblocking agent. The ammonia scavenger compound must also be sufficiently volatile to be capable of being stripped from the PSA composition at the temperatures at which the composition is being processed (typically 80° C. to 160° C.). The ammonia scavenger compound appears to work synergistically with the added water to greatly increase lap shear stability, particularly the resistance to creep measured in accordance with the stringent procedure set out in U.S. MIL-T-81287, of silicone PSAs of U.S. Pat. No. 4,591,622 and therefore appears to be efficient at removing ammonia which is one factor that can reduce lap shear stability. Very small amounts of ammonia scavenger compounds such as about 0.001 parts per 100 parts of total resin copolymer (i) and polydiorganosiloxane (ii) appear to greatly increase the lap shear stability while the use of more than about 10 parts of the compound is believed to be wasteful. Since the silicone PSAs are to be used in a medical device, it is best to use adhesives which are as free as possible of non-critical by-products such as ammonia or reactants and catalysts used to manufacture such adhesives.

Examples of ammonia scavenger compounds are those such as alcohols of the formula $HOC_mH_{2m+1}$ where m has a value of from 2 to 4 such as ethanol, iso-propanol, n-butanol and isobutanol; glycol ethers of the formula $HOC_xH_{2x}(OC_xH_{2x})_y(O)_vH$ where x has a value of from 2 to 6, y has a value of from 0 to 3 and v has a value of 0 or 1 such as ethylene glycol, propylene glycol, hexylene glycol, $HOCH_2CH_2OCH_2CH_3$, $HO(CH_2)_{60}(CH2)_6OH$, and $HO(CHCH_3CH_2O)_3H$; ethers of the formula having the formula $C_wH2_{w+1}(OC_xH_{2x})_yOC_wH_{2w+1}$ where w has a value of from 1 to 3 and x and y are as above such as $C_2H_5OC_2H_5$, $C_2H_5OCH_2CH_2OC_2H_5$, $C_2H_5O(CHCH_3CH_2)OC_2H_5$, $C_4H_9O(CHCH_3CH_2)OC_4H_9$, $C_2H_5O(CH_2CH_2O)_3C_2H_5$, and $C_2H_5O(CH_2CH_2O)_2C_2H_5$; esters of the formula $CwH2w+1C(O)OCnH2n+1$ and $HC(O)OC_nH_{2n+1}$ where w and n are as defined above such as methyl acetate, ethyl acetate, propyl acetate, amyl acetate, hexylacetate, ethyl formate and ethyl propionate. Most preferred as an ammonia scavenger compound are alcohols. Primary alcohols may be more effective than secondary alcohols followed by tertiary alcohols. Isopropanol, a secondary alcohol, was found to be effective. Just as water alone improves lap shear stability preferably by removing ammonia, the ammonia scavenger compounds alone are expected to improve lap shear stability by removing ammonia.

In accordance with the above preferred U.S. Pat. No. 4,584,355 or U.S. Pat. No. 4,585,836 methods in Step (I) the resin copolymer (i) and polydiorganosiloxane (ii), are mixed together with water alone or with water and the ammonia scavenger compound and any organic solvent that is to be added. To accomplish effective removal of the ammonia generated by endblocking agent (iii), the preferred method involves conducting the condensation reaction of (i), (ii) and (iii) with heating at 80° C. to 160° C. and, more preferably, at 100° to 120° C. Thus, after (i), (ii), the water or the water and ammonia scavenger, the condensation catalyst (iv) and the organic solvent are mixed together, the ammonia generating endblocking agent (iii) is added to the mixture. If one is used, a condensation catalyst (iv) for the endblocking reaction such as trifluoroacetic acid is added after the endblocking agent (iii). The mixture is stirred at room temperature to insure that all ingredients are mixed well. To simplify the procedure, the water or the water and ammonia scavenger compound can be added at the beginning of the procedure although these ingredients could be added at any point during or after the hereinafter-described condensation step (II) since the function of these ingredients is to remove the ammonia from the PSA composition being made. For example, the water or water and ammonia scavenger compound may also be added just prior to the hereinafter-described additional stripping step (III). This may require cooling of the mixture before the lower boiling water and in some cases, the ammonia scavenger compound (when used), can be added. If a condensation catalyst (iv) for the endblocking reaction is to be used, it should be added after the addition of endblocking agent (iii), but before the hereinafter described condensation step (II).

The condensation step (II) is begun when addition of an ammonia generating endblocking agent (iii) is made at room temperature. Condensation continues when the mixture is heated from 80° C. to 160° C., preferably to 100 and 120° C. Condensation is preferably allowed to proceed at least until the rate of evolution of condensation by-products such as water is substantially constant. Heating is then continued until the desired physical properties such as viscosity, tack and adhesion values are obtained. Typically the mixture is allowed to reflux for an additional 1 to 4 hours after the rate of evolution of condensation by-products is substantially constant. Longer condensation times may be needed for compositions containing organofunctional radicals such as fluorinated radicals on the polydiorganosiloxane (ii) or endblocking agent which are less compatible with those on the resin copolymer (i). During the condensation step and the additional reflux step, condensation by-products are at least periodically removed from the mixture such as by azeotropic removal of by-products or by removing some solvent periodically from the mixture.

Presently, the preferred procedure used when ammonia scavenger compounds are employed (to obtain optimal removal of ammonia from the adhesive composition) is to add the water, the endblocking agent and any condensation catalyst (iv) together with (i) and (ii) and to conduct the condensation step (II) described above. When that Step (II) is complete, the ammonia scavenger compound is added and the reaction product is held at reflux temperature for a period of time (3 hours is presently preferred although 1–5 hours can also be adequate) to improve removal of ammonia during stripping before the stripping Step (III) is started. This procedure appears to optimize removal of ammonia from the reaction mixture.

When the condensation reaction of U.S. Pat. No. 4,584, 355 or 4,585,836 is substantially complete, Step (III) is begun wherein the residual endblocking agent, water or water and ammonia scavenger compound, and any remaining ammonia is solvent stripped away by removing excess solvent during or after the step (II) involving azeotropic removal of condensation by-products. Removal of solvent will carry away more volatile ingredients as part of the solvent or as separate ingredients which are carried with the solvent during stripping. The nonvolatile solids content of the resulting silicone PSA composition can be modified as described, supra. Likewise, a precondensation step of the type described, supra, can be employed prior to carrying out condensation in the presence of the above-described ammonia-generating endblocking agents. Since it is desirable to remove as much volatile material as possible for adhesives to be used in medical products, the U.S. Pat. No. 4,584,355, and 4,585,836 processes are presently preferred as described above.

In a less preferred, but possibly useful alternative silicone PSA composition, the resin copolymer (i) described previously can be condensed with the aforementioned endblocking agents to minimize the level of silicon-bonded hydroxyl content therein. This chemically treated resin copolymer can then simply be cold-blended or further heated with a high molecular weight polydiorganosiloxane gum of the type described as polydiorganosiloxane (ii) to obtain a PSA composition wherein the silicon-bonded hydroxyl radical content is minimal because the primary source of silicon-bonded hydroxyl content is from the resin copolymer (i) which has been chemically treated and the silicon-bonded hydroxyl radical content of the high molecular weight polydiorganosiloxane is very low since such radicals will only be found at the terminal siloxy units.

The silicone PSA compositions described above can be used as prepared to prepare PSA films for use on transdermal drug delivery devices in accordance with well-known techniques or else can, optionally, be further cured to increase the cross-link density of the adhesive film to improve the physical properties of the film. Uncured adhesives generally do not have cohesive strengths which are as high as those exhibited by cured adhesives. In accordance with well-known procedures, about 0.5–3% by weight of a peroxide catalyst such as benzoyl peroxide or 2,4-dichlorobenzoyl peroxide based on adhesive solids can be added to the composition and the film can be cured at 110° C. to 200° C. for 1 to 10 minutes. Other free radical cross-linking methods such as electron beam or actinic radiation may be useful in curing adhesive films, particularly when the silicone PSA contains aliphatically unsaturated radicals such as vinyl radicals. When the resin copolymer (i) and/or the endblocking triorganosilyl units of (iii) of the silicone PSA contain aliphatically unsaturated radicals such as vinyl radicals, the adhesive can be cured at room temperature or by heating by using an SiH bearing coreactant in conjunction with a chloroplatinic acid catalyst in the well-known manner.

If desired, the silicone PSAs of this invention can be combined or blended with other adhesives including, for example, other silicone adhesives or other organic adhesives. For instance, the adhesives of this invention can be blended with organic adhesives such as acrylics including, for example those with no functionality or those with OH or COOH functionality, or rubber adhesives such as natural rubber, polyisobutylene or polybutadiene. These blends could be, for example, in weight ratios of silicone PSAs of this invention to other adhesives of 10:90 to 90:10.

Other well-known ingredients such as fillers or pigments may be added to the silicone PSA compositions used in the present invention provided that such materials do not adversely affect the adhesive properties of the compositions and/or the biocompatibility of the adhesive. It is also anticipated that cold blends of two or more silicone PSA compositions may be made to obtain compositions having intermediate properties. For example, a silicone PSA composition having 70–90 parts of resin copolymer (i) and 10–30 parts of polydiorganosiloxane (ii) having a high adhesion value (e.g., ≧1300 g/inch) can be blended with a silicone PSA composition of the present invention to improve the adhesion value of the silicone PSA composition. It is preferred that the modifier be chemically treated as described above. Use of modifiers containing significant levels of silicon-bonded hydroxyl content can result in an adhesive which loses its tack to an unacceptable degree. The modifier need not be a PSA and can comprise from 1 to 100 parts by weight of copolymer (i) and 0 to 99 parts by weight of polydiorganosiloxane (ii).

Having described silicone PSA compositions useful in the present invention, one skilled in the art can then construct the improved transdermal drug delivery devices using such compositions so that the device can be maintained in contact with the skin of a wearer for a longer period of time than is generally the case for silicone PSAs which were not chemically treated as described above. Transdermal drug delivery devices of the present invention can also be expected to have a longer shelf life because the adhesive does not lose as much of its tack and ability to instantly adhere to the skin upon storage as do untreated compositions of the same type. The same compositions which have not been chemically treated typically lose tack and ability to instantly adhere to the skin with time since in most devices the drug begins to migrate from the controlled release means immediately upon construction of the device and thereby contacts the adhesive.

The following Examples are illustrative only and should not be construed as limiting the invention which is properly delineated in the appended claims. In the following Examples, all parts and percentages are by weight unless otherwise specified.

Test Procedures

The nonvolatile solids content (NVC) of a material was determined by placing 3–5 grams (A) of the material in an aluminum foil dish, 60 mm in diameter and 15 mm deep, and heating the sample for 1 hour at 200° C. in an air-circulating oven. The heated sample was then cooled to room temperature and reweighed to determine the weight of the nonvolatile material (B). The NVC, in percent, is equal to 100*B/A.

The solution viscosity of a material was determined at 25° C. with a Brookfield® Viscometer Model RVT using spindle #5 at 20 rpm.

The silicon-bonded hydroxyl content was determined using $^{29}$Si Nuclear Magnetic Resonance and Fourier Transform Infrared spectroscopy techniques. A relationship between the $^{29}$Si NMR data and FTIR data was established. For the $^{29}$Si NMR spectroscopy, the samples were prepared at approximately 50 volume % in $CDCl_3$ with 0.04 M Chromium(III)acetylacetonate to ensure quantitative conditions. Solution state $^{29}$Si NMR spectroscopy was performed on a Varion 400 MHz NMR spectrometer with a 16 mm probe tuned to 79.458 MHz. Gated decoupling, a 45° pulse width of 13.0 us, and a relaxation delay time (at+d1) of 4.6 s (at=1.6 s, d1=3 s) were used. 1024 transients were signal-averaged to achieve an adequate signal/noise.

For the FTIR spectroscopy, samples were prepared by casting the adhesive solution onto an appropriate release liner and removing the solvent to form an adhesive film. The adhesive films were transferred to salt discs for analysis. Infrared spectra were measured using a Perkin-Elmer 1600 spectrophotometer. The background scans and spectral scans were completed with the following settings: absorbance mode, 16 scans, weak apodization, 4 $cm^{-1}$ resolution. The sample was scanned and the $A_1/(A_2*100)$ peak ratio calculated. The $A_1$ area corresponds to the peak for the dimeric elongation vibration of the O—H bond from the silanol group. The $A_2$ area corresponds to the area for an overtone peak of the deformation of the hydrogen of the polydimethylsiloxane (PDMS) methyl group.

Figure 1:
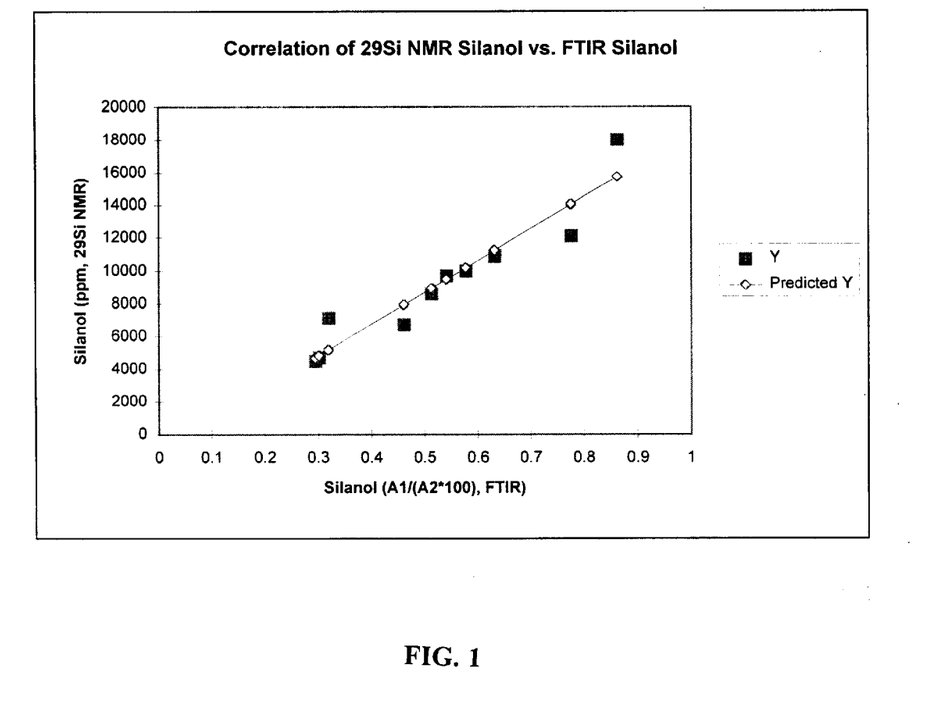

A series of adhesive samples of varying silicon-bonded hydroxyl content were analyzed via the $^{29}$Si NMR and FTIR spectroscopy techniques. A relationship was established (see FIG. 1) as follows:

$$\text{Silanol (ppm, }^{29}\text{Si NMR)} = 19426.6*[A1/(A2*100)] - 1029.2$$

The FTIR data were used to calculate ppm silanol content for the samples in the Examples. For blends of adhesives, the FTIR values were calculated by linear interpolation on a weight percent basis using the high silanol and low silanol values.

For the static shear testing, the samples are prepared as follows: The silicone adhesive solution, acrylic adhesive solution and drug are blended together. The mixture is solvent cast on appropriate release liner and the solvent is removed to form a dried adhesive layer. The cast film is then laminated to an appropriate backing film to form the final matrix composition. A strip of the adhesive matrix approximately 1.5 mil thick with 0.75"×0.50" contact area is attached to a stainless steel plate and placed in an oven at a 90° F. (to simulate skin temperature) for 30 minutes. A 1000 gram load is attached to the strip on the stainless steel plate which is positioned at a 2° angle from vertical. The angle eliminates peel effects to obtain shear data. The value reported is the time in minutes for the adhesive strip to completely pull away from the plate.

EXAMPLE 1

In this example, the silicon-bonded hydroxyl content of silicone PSAs was reduced by chemically treating with (CH3)3SiNH at various concentrations between 0.3–0.8 moles of silyl units/moles silanol groups.

Precondensation Step

A) 65 parts Resin (based on 100% solids) comprising trimethylsiloxy and hydroxy endblocked silicate resin in a three dimensional structure and 35 parts of hydroxy end-blocked polydimethylsiloxane with a viscosity of about 13,500 cp at 25 C. were blended together with sufficient xylene to yield a nominal 70% solids mixture. The mixture was placed in a 3-necked flask. The flask was equipped with a bottom discharge, thermometer, Dean-Stark trap fitted with a water-cooled condenser, a stirring paddle and a heating mantle.

Condensation Step

B) The mixture was heated to 115° C. A condensation catalyst, anhydrous ammonia was bubbled through the reaction mixture. The reaction was continued until a target solution viscosity at 25° C. was reached.

Partial Capping Reaction

C) A predetermined amount of the treating agent as shown in the following table, hexamethylsilazane, was added to the reactor vessel. The temperature was maintained at 115° C. temperature during the capping reaction. The capping reaction was continued until no change in silicon-bonded hydroxyl content was detected by the FTIR measurement.

Refluxing Step

D) The mixture was heated to 140° C. and reflux and remove any residual treating agent and ammonia. The refluxing is complete when the solution pH is neutral.

Devolatization Step

E) Devolatize on appropriate release liner. Store the adhesive in the oven until the solvent is removed.

Resolvation Step

F) Add sufficient ethyl acetate to achieve a 60% NVC solution. Roll the blending container until the mixture is homogenous.

The adhesive was then blended with acrylic adhesive and an amine moiety containing drug. The results in the following table show the silanol and shear data for variously capped adhesives.

| Adhesive No | Moles silyl units/ moles silanol groups | Calculated ppm Silanol | 24 hr Shear (1) (minutes) |
|---|---|---|---|
| 1 | 0 | 15406 | 51.0 |
| " | 0.32 | 13852 | 51.9 |
| " | 0.64 | 11987 | 44.8 |
| " | >1 | 7577 | 2.6 |
| 2 | 0 | 13385 | 102.5 |
| " | 0.37 | 12239 | 127.7 |
| " | 0.73 | 11268 | 86.4 |
| " | >1 | 6275 | <0.1 |
| 3 | 0 | 11948 | 155.2 |
| " | 0.41 | 10607 | 114.1 |
| " | 0.82 | 9772 | 86.7 |
| " | >1 | 5673 | 11.1 |

(1) Laminate aged 24 hours prior to testing.

EXAMPLE 2

In this example, the silicon-bonded hydroxyl content of silicone pressure-sensitive adhesives of Example 1 was reduced by preparing blends of capped (i.e., >1 Moles silyl units/moles silanol groups by method of U.S. Pat. No. RE35,474) and uncapped silicone pressure-sensitive adhesives (no treating agent) in combination with the acrylic adhesive and the amine moiety containing drug. The results are shown in the following table.

| Blend ratio of uncapped to capped adhesive | Calculated ppm Silanol | 24 hr Shear (2) (minutes) |
|---|---|---|
| 100:0 | 13230 | 58.9 |
| 90:10 | 12628 | 44.7 |
| 80:20 | 13832 | 25.8 |
| 70:30 | 13055 | 17.3 |
| 0:100 | 7577 | 2.6 |
| 100:0 | 13385 | 102.5 |
| 90:10 | 12667 | 90.3 |
| 80:20 | 11967 | 76.1 |
| 70:30 | 11248 | 40.7 |
| 0:100 | 6275 | <0.1 |
| 100:0 | 11948 | 155.2 |
| 90:10 | 11326 | 89.0 |
| 80:20 | 10685 | 90.3 |
| 70:30 | — | — |
| 0:100 | 5673 | 11.1 |
| 100:0 | 13230 | 58.9 |
| 90:10 | 12628 | 44.7 |
| 80:20 | 12045 | 41.6 |
| 70:30 | 11404 | 33.3 |
| 60:40 | 10840 | 28.9 |
| 50:50 | 10258 | 24.6 |
| 0:100 | 7266 | <0.1 |
| 100:0 | 14007 | 50.9 |
| 90:10 | 13366 | 36.3 |
| 80:20 | 12744 | 23.7 |
| 70:30 | 12103 | 39.5 |
| 0:100 | 7674 | 5.8 |

(1) Laminate aged 24 hours prior to testing.

The use of uncapped adhesive in the active matrix of these examples resulted in a laminate which had low initial tack. This is the result of the drug reacting with the uncapped adhesive. Although the laminate was shear rested, the resultant laminate could not be applied to skin for use as a device for any substantial duration of time.

The use of fully capped adhesive resulted in a laminate which had hign initial tack but lacked the cohesive properties necessary for use in transdermal drug delivery devices. The low shear values are indicative of what is known to those skilled in the art as oozing once a device is applied to the skin.

The use of partially capped adhesive resulted in laminate which had both good initial tack and cohesive strength.

It should be noted that the shear data is based on laboratory sample preparation. Although the values recorded are averages of n+3, some variation does exist in the laminate coat weights which may cause variation in the data.

That which is claimed is:

1. A transdermal drug delivery device for the controlled transdermal delivery of an active pharmaceutical agent comprising:
   (A) a drug delivery device comprising an active pharmaceutical agent and a means for its controlled delivery through the skin; and
   (B) a silicone pressure sensitive adhesive for maintaining contact between the device and the skin of a wearer, wherein the silicone pressure sensitive adhesive comprises:
      (i) between about 40 and about 70 parts by weight of at least one resin copolymer comprising triorganosiloxy units of the formula $R_3SiO1/2$ and tetrafunctional siloxy units of the formula $SiO_{4/2}$ in a ratio of about 0.6 to 0.9 triorganosiloxy units for each tetrafunctional siloxy unit, wherein each R independently denotes a monovalent hydrocarbon radical having from 1 to 6 carbon atoms; and
      (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms;
   wherein the silanol content of the silicone pressure sensitive adhesive composition has been reduced by chemically treating at least a portion of (i), (ii) or the mixture of (i) and (ii) with at least one chemical treating agent (iii) that reacts with silicon-bonded hydroxyl groups to reduce the silicon-bonded hydroxyl content of the composition to a range of between about 8000 and about 13000.

2. The device of claim 1 wherein the chemical treating was accomplished by blending
   (I) a composition comprising (i) from 40 to 70 inclusive parts by weight of at least one resin copolymer containing silicon-bonded hydroxyl radicals and comprising triorganosiloxy units of the formula $R_3SiO_{1/2}$ and tetrafunctional siloxy units of the formula $SiO_{4/2}$ in a ratio of about 0.6 to 0.9 triorganosiloxy units for each tetrafunctional siloxy unit present in the copolymer and (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms; and
   (II) a composition which has been chemically treated with at least one chemical treating agent that is reactive to silicon-bonded hydroxyl groups to reduce the silicon-bonded hydroxyl content of the composition comprising (i) from 40 to 70 inclusive parts by weight of at least one resin copolymer containing silicon-bonded hydroxyl radicals and comprising triorganosiloxy units of the formula $R_3SiO1/2$ and tetrafunctional siloxy units of the formula $SiO_{4/2}$ in a ratio of about 0.6 to 0.9 triorganosiloxy units for each tetrafunctional siloxy unit present in the copolymer and (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms.

3. The device of claim 1 wherein R in the pressure sensitive adhesive is methyl and the chemical treating agent (iii) is $(R_3Si)_2NH$.

4. The device of claim 1 wherein (i) is present at from 53 to 65 parts by weight and (ii) is present at from 35 to 47 parts by weight.

5. The device of claim 1 wherein the silicone pressure sensitive adhesive also contains a catalytic amount of a condensation catalyst.

6. A method of making a silicone-pressure sensitive adhesive composition for use on a transdermal drug deliver device comprising
   (I) mixing (i) between about 40 and about 70 parts by weight of at least one resin copolymer comprising triorganosiloxy units of the formula $R_3SiO_{1/2}$ and tetrafunctional siloxy units of the formula $SiO_{4/2}$ in a ratio of about 0.6 to 0.9 triorganosiloxy units for each tetrafunctional siloxy unit; and (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms; and
   (II) condensing the mixture of (i) and (ii) with a sufficient amount of a chemical treatment agent (iii) comprising at least one organosilicon endblocking agent capable of generating an endblocking triorganosilyl unit to reduce the silicon-bonded hydroxyl content of the composition to a range of between about 8000 and about 13000.

7. A silicone pressure sensitive adhesive composition comprising a blend of:
   (I) a composition comprising (i) from 40 to 70 inclusive parts by weight of at least one resin copolymer containing silicon-bonded hydroxyl radicals and comprising triorganosiloxy units of the formula $R_3SiO_{1/2}$ and tetrafunctional siloxy units of the formula $SiO_{4/2}$ in a ratio of about 0.6 to 0.9 triorganosiloxy units for each tetrafunctional siloxy unit present in the copolymer and (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms; and (II) a composition which has been chemically treated with at least one chemical treating agent that is reactive to silicon-bonded hydroxyl groups to reduce the silicon-bonded hydroxyl content of the composition comprising (i) from 40 to 70 inclusive parts by weight of at least one resin copolymer containing silicon-bonded hydroxyl radicals and comprising triorganosiloxy units of the formula $R_3SiO_{1/2}$ and tetrafunctional siloxy units of the formula $SiO_{4/2}$ in a ratio of about 0.6 to 0.9 triorganosiloxy units for each tetrafunctional siloxy unit present in the copolymer and (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms.

8. A transdermal drug delivery device comprising the silicone pressure sensitive adhesive of claim 7.

9. In a transdermal drug delivery device for the controlled transdermal delivery of an active pharmaceutical agent comprising an active pharmaceutical agent and a means for its controlled delivery associated therewith, said reservoir being adapted to hold said drug delivery means in close proximity to the skin of a wearer, said device having a silicone pressure-sensitive adhesive for maintaining contact between said container and the skin of a wearer, the improvement comprising the use of a silicone pressure sensitive adhesive comprising (i) between about 40 and about 70 parts by weight of at least one resin copolymer comprising triorganosiloxy units of the formula $R_3SiO_{1/2}$ and tetrafunctional siloxy units of the formula $SiO_{4/2}$ in a ratio of about 0.6 to 0.9 triorganosiloxy units for each tetrafunctional siloxy unit; and (ii) between about 30 and about 60 parts by weight of at least one polydiorganosiloxane comprising ARSiO units terminated with endblocking $TRASiO_{1/2}$ units, wherein the polydiorganosiloxane has a viscosity of from about 100 centipoise to about 30,000,000 centipoise at 25° C. and each R is as above, each A radical is independently selected from R or halohydro-carbon radicals having from 1 to 6 inclusive carbon atoms, each T radical is independently selected from the group consisting of R, OH, H or OR', and each R' is independently an alkyl radical of from 1 to 4 inclusive carbon atoms;

wherein the silanol content of the silicone pressure sensitive adhesive composition has been reduced by chemically treating at least a portion of (i), (ii) or the mixture of (i) and (ii) with at least one chemical treating agent (iii) that reacts with silicon-bonded hydroxyl groups to reduce the silicon-bonded hydroxyl content of the composition to a range of between about 8000 and about 13000.

* * * * *